United States Patent

Petersen et al.

[11] 4,149,948
[45] Apr. 17, 1979

[54] ELECTROCHEMICAL CELL FOR DETECTING HYDROGEN SULPHIDE IN A GASEOUS MIXTURE

[75] Inventors: Otto Petersen; Hans-Dieter Schmidt, both of Krefeld, Fed. Rep. of Germany

[73] Assignee: Bayer Aktiengesellschaft, Leverkusen, Fed. Rep. of Germany

[21] Appl. No.: 852,752

[22] Filed: Nov. 18, 1977

[30] Foreign Application Priority Data

Dec. 18, 1976 [DE] Fed. Rep. of Germany ....... 2657570

[51] Int. Cl.² ............................................. G01N 27/46
[52] U.S. Cl. .............................. 204/195 R; 204/195 P; 204/1 T
[58] Field of Search ................... 204/1 T, 1 F, 195 R, 204/195 P, 195 S

[56] References Cited

U.S. PATENT DOCUMENTS

| 333,292 | 12/1885 | Fitzgerald et al. | 429/228 |
| 3,857,760 | 12/1974 | Breuer et al. | 204/195 S |
| 4,029,563 | 6/1977 | Binder et al. | 204/1 F |
| 4,049,503 | 9/1977 | Becker et al. | 204/1 F |

OTHER PUBLICATIONS

Ives et al., "Reference Electrodes", 1961, pp. 381–383.

*Primary Examiner*—T. Tung
*Attorney, Agent, or Firm*—Sprung, Felfe, Horn, Lynch & Kramer

[57] ABSTRACT

An electrochemical cell suitable for detecting traces of hydrogen sulphide in a gaseous mixture. Silver / silver sulphide electrodes are embedded in a polarographic arrangement in a gel-like electrolyte wherein the film adjacent to the auxiliary electrode contains a depolarizer. The gas detector is characterized by freedom from the need for maintenance and a high sensitivity which remains constant for a long period.

3 Claims, 1 Drawing Figure

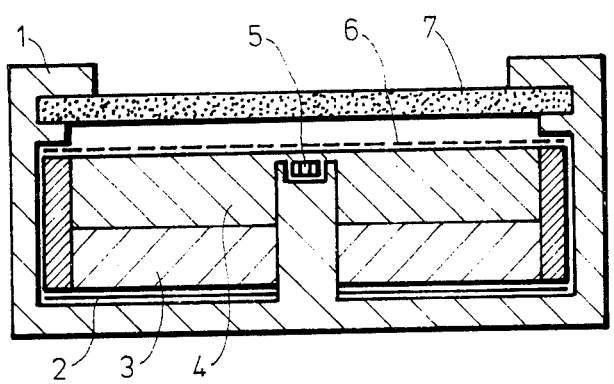

ELECTROCHEMICAL CELL FOR DETECTING HYDROGEN SULPHIDE IN A GASEOUS MIXTURE

The invention relates to an electrochemical cell for detecting hydrogen sulphide in a gaseous mixture, the cell having three electrodes (a work electrode, a reference electrode and an auxiliary electrode) in a polarographic arrangement in an organic, electrically conductive electrolyte.

Electrochemical cells for detecting a gas in a gaseous mixture are particularly important in the field of pollution control. They have to determine when dangerous concentrations are exceeded and they must therefore be sensitive without maintenance and constantly operating for a prolonged period of time. An electrochemical cell is described in our copending U.S. application Ser. No. 804,699 in which the work and reference electrodes are either silver/silver iodide electrodes or silver/silver chloride electrodes, the auxiliary electrode is made of silver, and the electrolyte is a slightly alkaline organic electrolyte. The cell described in that patent application has the disadvantage that the sensitivity of the cell diminishes with time since the auxiliary electrode is passivated as a result of hydrogen elimination and the alternation of the work electrode.

The object of the invention is to provide an electrochemical cell for detecting hydrogen sulphide in a gaseous mixture in which the sensitivity changes as little as possible with time.

According to the invention, there is provided an electrochemical cell for detecting hydrogen sulphide in a gaseous mixture, the cell comprising a work electrode, a reference electrode and an auxiliary electrode in a polarographic arrangement in an organic electrically conductive electrolyte, wherein the work electrode and the reference electrode are silver/silver sulphide electrodes and the electrolyte comprises two gel-like films one of which is adjacent the auxiliary electrode, the two films being of identical composition except that the film adjacent the auxiliary electrode contains a depolarizer.

In these electrochemical cells, the cathode (auxiliary electrode) is not passivated. The sensitivity is more nearly constant when using silver/silver sulphide electrodes, than when using the hitherto conventional silver iodide or silver chloride electrodes, since in the former case there is a gradual partial conversion into silver sulphide.

In an advantageous embodiment, the auxiliary electrode is a copper foil and it is surrounded with an electrolyte containing lead dioxide or another heavy metal oxide of high valence. The nascent hydrogen formed is oxidised to produce water and the auxiliary electrode is not passivated. This may be ascertained by the fact that the internal resistance of the cell does not increase.

The electrolyte preferably comprises a mixture of polyvinyl chloride, propylene carbonate, diethyl phthalate and potassium hexafluorophosphate. It has a gel-like consistency and does not separate even after a long period of operation. A suitable mixture is composed of for example 10 to 20%, preferably 16%, by weight of polyvinyl chloride, from 20 to 30%, preferably 28%, by weight of propylene carbonate, from 50 to 60%, preferably 55%, by weight of diethyl phthalate and 1% by weight of potassium hexafluorophosphate.

An electrochemical cell according to the invention is shown in the drawing by way of example and is described in more detail below.

A copper auxiliary electrode 2 rests on the base of a cylindrical container 1 made of polypropylene. An electrolyte 3 directly above the auxiliary electrode is composed of the above-mentioned mixture and additionally contains from 2 to 10%, preferably about 5%, by weight of lead oxide.

The electrolyte is a gel-like film having the consistency of soft rubber and is pressed against the copper auxiliary electrode. An electrolyte film 4 which is free of lead dioxide is pressed upon this electrolyte. The electrolyte film 4 has a silver/silver sulphide reference electrode 5 of spiral form. A reticular silver/silver sulphide work electrode 6 is pressed when warm into the electrolyte from above. The cell is sealed by means of a glass frit 7. A volume of gas which is about 1 mm thick remains between the frit 7 and the work electrode 6. Gas exchange takes place by diffusion and a forced gas supply is not required.

What we claim is:

1. An electrochemical cell for detecting hydrogen sulphide in a gaseous mixture comprising a work electrode, a reference electrode, an auxiliary electrode and an organic electrically conductive electrolyte, said work electrode and said reference electrode being silver/silver sulphide electrodes and the electrolyte comprising two gel-like films one of which is adjacent the auxiliary electrode and the other of which having the reference and work electrodes therein, the two films being of identical composition except that the film adjacent the auxiliary electrode contains a depolarizer.

2. An electrochemical cell according to claim 1, wherein the electrolyte is composed of from 10 to 20% by weight of polyvinyl chloride, 20 to 30% by weight of propylene carbonate, from 50 to 60% by weight of diethyl pththalate and about 1% by weight of potassium hexafluorophosphate.

3. An electrochemical cell according to claim 2, wherein the film adjacent the auxiliary electrode contains from 2 to 10% by weight of lead dioxide or said depolarizer.

* * * * *

UNITED STATES PATENT AND TRADEMARK OFFICE
CERTIFICATE OF CORRECTION

PATENT NO. : 4,149,948
DATED : April 17, 1979
INVENTOR(S) : OTTO PETERSEN et al

It is certified that error appears in the above-identified patent and that said Letters Patent are hereby corrected as shown below:

Column 2, line 54, "or" should be --as--.

Signed and Sealed this

Second Day of October 1979

[SEAL]

Attest:

RUTH C. MASON
Attesting Officer

LUTRELLE F. PARKER
Acting Commissioner of Patents and Trademarks